US005519532A

United States Patent [19]
Broome

[11] Patent Number: 5,519,532
[45] Date of Patent: May 21, 1996

[54] DISPOSABLE ENDOSCOPE

[75] Inventor: Barry G. Broome, Glendora, Calif.

[73] Assignee: Linvatec Corporation, Largo, Fla.

[21] Appl. No.: 223,409

[22] Filed: Apr. 4, 1994

Related U.S. Application Data

[63] Continuation of Ser. No. 833,416, Feb. 6, 1992, Pat. No. 5,341,240.

[51] Int. Cl.$^6$ .............................. G02B 21/02; A61B 1/04
[52] U.S. Cl. .......................... 359/435; 359/434; 359/656
[58] Field of Search .................................. 359/362–363, 359/423–424, 434–435, 643–645

[56] References Cited

U.S. PATENT DOCUMENTS

| | | | |
|---|---|---|---|
| 1,741,575 | 12/1919 | Leiter | 128/7 |
| 1,915,811 | 6/1933 | Wolf | 128/7 |
| 2,406,762 | 9/1946 | Grey | 359/765 |
| 2,453,218 | 11/1948 | Grey | 359/795 |
| 2,519,760 | 8/1950 | Hett | 359/367 |
| 2,571,308 | 10/1951 | Taylor | 359/794 |
| 2,899,862 | 8/1959 | Baker | 359/435 |
| 3,257,902 | 6/1966 | Hopkins | 359/435 |
| 3,380,335 | 4/1968 | Clave et al. | 356/22 |
| 3,468,598 | 9/1969 | Ito | 359/435 |
| 3,583,785 | 6/1971 | Boardman | 359/435 |
| 3,625,583 | 12/1971 | Beiser | 359/5 |
| 3,836,249 | 9/1974 | Weber | 355/51 |
| 3,936,149 | 2/1976 | Imai | 359/654 |
| 4,025,155 | 5/1977 | Imai | 359/435 |
| 4,036,218 | 7/1977 | Yamashita et al. | 128/4 |
| 4,076,018 | 2/1978 | Heckele | 128/6 |
| 4,086,000 | 4/1978 | Cox et al. | 359/434 |
| 4,138,192 | 2/1979 | Yamashita | 359/726 |
| 4,140,364 | 2/1979 | Yamashita et al. | 359/367 |
| 4,149,769 | 4/1979 | Zobel | 359/432 |
| 4,165,917 | 8/1979 | Yamashita et al. | 359/784 |
| 4,168,882 | 9/1979 | Hopkins | 359/434 |
| 4,195,904 | 4/1980 | Yamashita | 359/367 |
| 4,354,730 | 10/1982 | Bel | 359/434 |
| 4,385,810 | 5/1983 | Hamon | 359/381 |
| 4,398,811 | 8/1983 | Nishioka et al. | 359/367 |
| 4,500,181 | 2/1985 | Takahashi | 359/503 |
| 4,501,477 | 2/1985 | Sunaga | 359/380 |
| 4,515,444 | 5/1985 | Prescott et al. | 359/654 |
| 4,545,652 | 10/1985 | Hoogland | 359/715 |
| 4,575,195 | 3/1986 | Hoogland | 359/716 |
| 4,624,243 | 11/1986 | Lowery et al. | 128/6 |

(List continued on next page.)

FOREIGN PATENT DOCUMENTS

| | | |
|---|---|---|
| 1018091 | 5/1983 | U.S.S.R. . |
| 1277496 | 6/1972 | United Kingdom . |
| 1433150 | 7/1976 | United Kingdom . |

OTHER PUBLICATIONS

A. I. Molev, in "A rod–like optical system for endoscopes", Biomedical Engineering (a translated Russian language journal) vol. 9, No. 4, pp. 206–209 (Jul.–Aug. 1975).

Moore et al, "Third–Order Aberrations of Inhomogeneous Lenses with Cyclindrical Index Distributions", *Journal of the Optical Society of America*, vol. 61, No. 9. (1971).

*The Handbook of Plastic Optics*, 2nd Edition, published by U.S. Precision Lens Co. of Cincinnati, Ohio (1983).

*Primary Examiner*—Thong Q. Nguyen
*Attorney, Agent, or Firm*—Michael de Angeli

[57] ABSTRACT

An endoscope includes a disposable probe and a non-disposable focusing ocular. The probe includes a transfer module assembly including one or more relay modules, and an objective element including a distal glass window, a molded plastic prism and three molded plastic lenses. Each of the relay modules contains an entry glass rod, an intermediate glass rod, and an exit rod, each having flat end surfaces and two identical molded plastic doublets. The elements of the ocular are all of glass and include an axially movable focusing doublet and two non-movable doublets. The disposable probe introduces certain aberrations into the image. The non-disposable focusing ocular corrects these aberrations. A single curved surface is formed on the distal glass window of the probe; all other curved optical surfaces of the disposable probe are formed on molded plastic members, thereby reducing the cost of the probe sufficiently to be cost-effective for single patient, disposable use.

13 Claims, 5 Drawing Sheets

U.S. PATENT DOCUMENTS

| | | | |
|---|---|---|---|
| 4,641,927 | 2/1987 | Prescott et al. | 359/654 |
| 4,655,557 | 4/1987 | Takahashi | 359/735 |
| 4,662,728 | 5/1987 | Whitehead | 359/435 |
| 4,671,630 | 6/1987 | Takahashi | 359/503 |
| 4,676,606 | 6/1987 | Takahashi | 359/754 |
| 4,684,224 | 8/1987 | Yamashita et al. | 359/735 |
| 4,693,568 | 9/1987 | Takahashi | 359/772 |
| 4,720,178 | 1/1988 | Nishioka et al. | 359/431 |
| 4,723,843 | 2/1988 | Zobel | 359/435 |
| 4,730,909 | 3/1988 | Takahashi | 359/735 |
| 4,735,491 | 4/1988 | Takahashi | 359/652 |
| 4,742,818 | 5/1988 | Hughes et al. | 128/6 |
| 4,746,203 | 5/1988 | Nishioka et al. | 359/834 |
| 4,755,029 | 7/1988 | Okabe | 359/654 |
| 4,783,154 | 11/1988 | Takahashi | 359/648 |
| 4,783,156 | 11/1988 | Yokota | 359/736 |
| 4,805,971 | 2/1989 | Fantone | 359/354 |
| 4,815,833 | 3/1989 | Zobel et al. | 359/726 |
| 4,838,247 | 6/1989 | Forkner | 128/6 |
| 4,859,040 | 8/1989 | Kitagishi et al. | 359/652 |
| 4,895,433 | 1/1990 | Takahashi et al. | 359/654 |
| 4,907,868 | 3/1990 | Kitagishi et al. | 359/557 |
| 4,916,534 | 4/1990 | Takahashi et al. | 348/67 |
| 4,930,880 | 6/1990 | Miyauchi | 359/653 |
| 4,946,267 | 8/1990 | Hoogland | 359/737 |
| 4,964,710 | 10/1990 | Leiner | 359/434 |
| 5,054,897 | 10/1991 | Ozawa | 359/691 |
| 5,094,004 | 11/1991 | Matsumura | 33/338 |
| 5,142,410 | 8/1992 | Ono et al. | 359/435 |
| 5,188,092 | 2/1993 | White | 128/4 |
| 5,341,240 | 8/1994 | Broome | 359/435 |
| 5,359,453 | 10/1994 | Ning | 359/435 |
| 5,416,638 | 5/1995 | Broome | 359/656 |

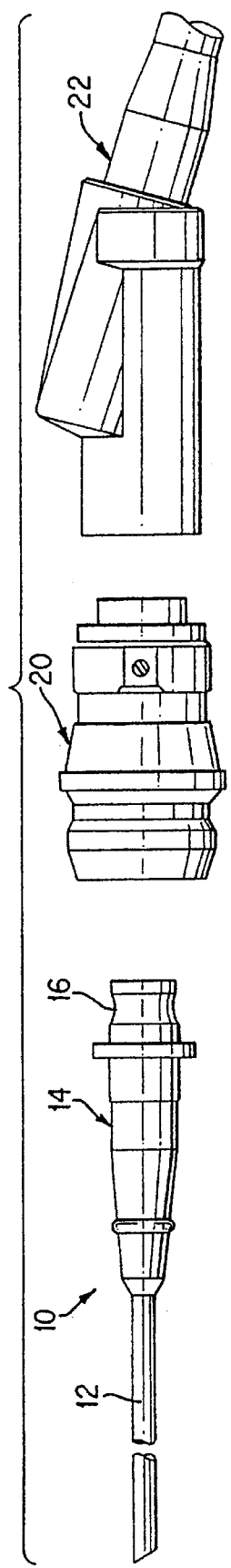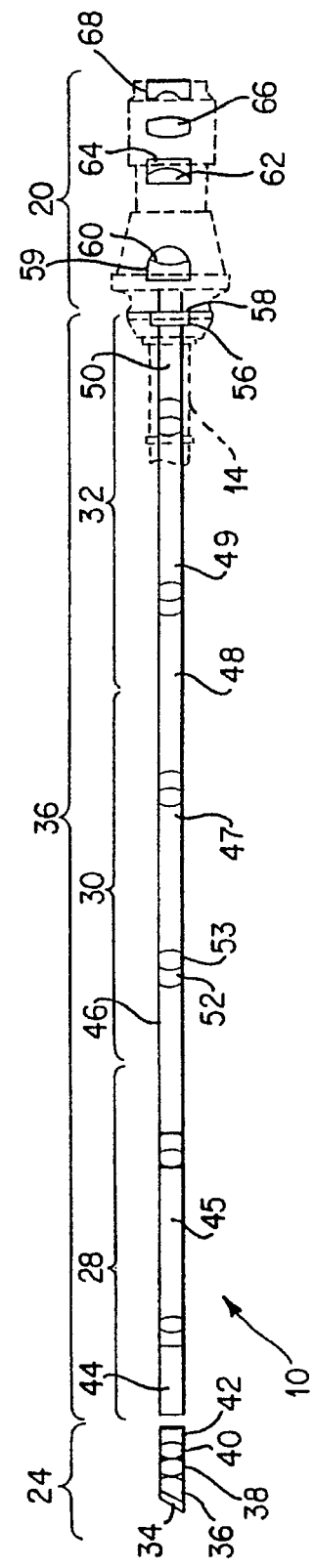
FIG. 1
FIG. 2

DISPOSABLE ENDOSCOPE

This application is a continuation of application Ser. No. 07/833,416, filed Feb. 6, 1992, now U.S. Pat. No. 5,341,240.

BACKGROUND OF THE INVENTION

1. Field of the Invention

The present invention relates to endoscopes and, more particularly, to endoscopes manufacturable sufficiently inexpensively to be disposable after single patient use, while being at least equal in optical performance to conventional endoscopes requiring sterilization.

2. Description of the Prior Art

Endoscopic or least invasive surgery has many advantages over conventional "open" surgery. Patients who have undergone endoscopic surgery rather than open surgery experience vastly less trauma and much faster recoveries, leading to improvement in the quality of health care together with reduction in the cost of health care. These advantages have spurred extensive development of endoscopes.

The term "endoscope" as used herein refers to an elongated optical probe capable of presenting a visible image of the interior of a body cavity, joint, organ or the like to a physician on either an eyepiece or a video screen. The endoscope is typically introduced into the body cavity through a bore in another device (also typically referred to in the art as an endoscope, or as an endoscope sheath) including a light source as well as other bores for introducing surgical instruments, water, air, suction and the like. Endoscopes as optimized for various surgical procedures are referred to as arthroscopes, cystoscopes, proctoscopes, laparoscopes and the like.

The art has for some years sought to develop a suitable disposable endoscope. The surgical requirement of absolute sterility is difficult to satisfy with conventional endoscopes as these complex instruments are not readily amenable to conventional sterilization techniques. The spread of infectious disease is of particular concern and requires that care and caution be employed during the sterilization process. Accordingly, there is a strong need for a suitable disposable endoscope, that is, one made sufficiently inexpensively as to be cost-effective for disposal after single-patient use.

Endoscopes typically consist of a distal objective for forming an optical image of the interior of the body cavity, bone, joint or organ, a transfer module (sometimes termed a "relay section") for transmitting the image from the distal end of the probe to its proximal end, and an ocular at the proximal end of the transfer module for presenting the image to an eyepiece, a video camera or the like. Typically, the ocular will contain the movable focusing components of the endoscope.

One of the difficult tasks in designing a satisfactory endoscope is that of designing the transfer module. The transfer module must be capable of transmitting the image formed by the objective to the ocular without significant loss of brightness or sharpness in the image. Early designs included numerous glass refractive elements, each requiring extensive polishing. The high cost of manufacture precluded use of these designs for disposable endoscopes.

More recently it has been suggested that the refractive optical elements of the transfer module should be molded of plastic, while the transmitting elements could be formed of much less expensive plano glass rods, i.e. glass rods having flat ends. Indeed, provision of the curved surfaces in optical systems by employment of molded plastic members, and using glass only for flat surfaced elements, is suggested by optical design textbooks; see, e.g., *The Handbook of Plastic Optics*, 2nd edition, published by U.S. Precision Lens, Inc. (1983), at page 86. However, despite this suggestion, there is no prior art disclosure or teaching of an endoscope providing adequate optical performance capable of manufacture at sufficiently low cost to be disposable.

Prior art endoscopes have typically been designed such that the objective provides a self-corrected image to the transfer module, the image then being transmitted with as little further aberration as possible to an ocular group. It is also known to employ the transfer module to correct aberration introduced by the objective. In either case the image presented by the probe to the objective is fully corrected. Typically the ocular designs employed have included two doublets placed back to back; this form permits separating the doublets at an afocal space. The first doublet is employed as a simple magnifier of the image, and the second doublet as a focusing element to allow a video camera to form the visible image on a display screen. However, this essentially simplified ocular design requires the image formed by the combination of the objective and the transfer module to be self-corrected. The cost of manufacture of suitable objective and transfer module components is too great for single patient disposable use.

Prior endoscopes have commonly also employed a fore-oblique prism in the tip of the endoscope to provide an off-axis field of view, that is, centered about an axis at an angle to the optical axis of the probe, so that by rotating the probe the surgeon has an effectively wider field of view than otherwise possible. In the prior art, such fore-oblique prisms have been manufactured by separately manufacturing two or three prisms of glass of high refractive index, separately coating the appropriate surfaces with reflective material, bonding the prisms together in an assembly jig requiring very high precision, and finally grinding the outer surface of the assembly to the desired cylindrical form. These manufacturing steps are very labor intensive and time-consuming, and render such fore-oblique prisms in the prior art much too expensive for use in a disposable device for single patient usage.

Another constraint on endoscope design arises because from time to time during surgery the surgeon may wish to change the endoscope's viewing angle, that is, to vary the angle between the center of the field of view and the optical axis of the probe. While endoscope designs have been proposed permitting variation of the viewing angle by moving a pivoted mirror or the like at the distal tip of the endoscope, these designs have been highly impractical. Variation of the viewing angle is possible in practical endoscopes only by removing a first probe from the surgical portal and substituting a second probe having a different viewing angle. To do so employing conventional re-usable endoscopes requires sterilization of several different endoscopes at substantial cost. If a video camera were being used to display the image, as is typical, this procedure would normally also necessitate disconnecting the ocular of the first endoscope from the video camera and reconnecting a second endoscope. It would be desirable to provide disposable endoscope probes having differing viewing angles all mating with the same nondisposable ocular, so that the probe could be replaced conveniently and discarded at reasonable cost if the surgeon desired to change viewing angles.

Endoscopic objectives found in the prior art have required glass elements of very high refractive index and having large differences in their spectral dispersion to provide control of optical aberration. These prior art designs have been limited to all-spherical surface design forms because of the cost of producing aspheric surfaces in glass. More specifically, one prior art endoscope objective design form uses a piano-concave flint glass element of very high refractive index preceding the prism element, a high index of refraction convex crown glass element bonded to the preceding prism element, a high index of refraction biconvex crown glass element, and a doublet including one element each of crown and flint glass. In the prior art, the high cost of production of these elements, having optical surfaces sufficiently steep to require individual polishing, had precluded use of this design for a disposable endoscope.

Until the present invention, there has been provided no design for an endoscope including a disposable probe that provides satisfactory optical performance, including convenient variation of viewing angle, while being manufacturable sufficiently inexpensively to be cost-effective for single-patient disposable use.

SUMMARY OF THE INVENTION

It is an object of the present invention to overcome the above-mentioned disadvantages of prior art disposable endoscopes.

More particularly, it is an object of the invention to provide an endoscope capable of providing a satisfactory visual or video image to a surgeon of the interior of a body cavity, bone, joint, vessel or organ, and including a probe manufacturable sufficiently inexpensively to be cost-effective for disposability after single-patient use.

It is a particular object of the invention to provide an objective design for an endoscope having its principal optical elements molded of plastic, and to thus greatly lower the cost of the endoscope as compared to prior art designs.

It is a further object of the invention to provide a disposable endoscope probe and, in particular, a disposable endoscope probe comprising a prism for providing oblique viewing angles requiring no complex and time-consuming assembly operations.

It is an object of the present invention to provide a transfer module for an endoscope that does not employ long glass rods but employs only short glass rods, rendering the device much less susceptible to breakage.

It is an object of the invention to provide an endoscope featuring essentially interchangeable disposable probes used with the same ocular and, in particular, to provide a selection of disposable probes having various viewing angles between the center of the field of view and the axis of the probe.

It is another object of the invention to provide a number of probes for an endoscope, each probe providing a different viewing angle, the probes differing only in the design of the prism but using essentially common components elsewhere, thus substantially economizing probe manufacture.

It is a further object of the invention to provide an endoscope comprising a disposable probe, including an objective group and a transfer module assembly, and a non-disposable ocular.

It is a further objective of the invention to provide an endoscope comprising a disposable probe and a non-disposable focusing ocular, wherein certain residual aberration is present in the image formed by the disposable probe and transferred to the ocular, and wherein the non-disposable ocular corrects the residual aberration in the image formed by the probe.

The above objects of the invention and needs of the art are satisfied by the present invention of an endoscope comprising a disposable probe and a non-disposable focusing ocular. The disposable probe is sufficiently inexpensive to be cost-effective for disposability after single patient use. The endoscope of the invention suffers no performance disadvantage compared to conventional non-disposable endoscopes.

The disposable probe of the present invention comprises an objective group at its distal end and a transfer module assembly. The objective group comprises a single glass window element at its distal end, a molded plastic prism and three molded plastic elements. The transfer module assembly comprises a number of identical relay modules. In the preferred embodiment, each relay module comprises two doublets with interspersed plano-surfaced glass rods. The doublets each include two molded plastic elements. The disposable probe introduces certain residual aberrations into the image presented to the non-disposable focusing ocular of the endoscope. The focusing ocular corrects for these aberrations, and optically couples the disposable probe to a video camera or the like.

The focusing ocular comprises a first movable focusing doublet and four further lens elements, all of glass. Relatively steep spherical surfaces are formed in these lens elements to correct chromatic aberration, field curvature, and astigmatism in the image presented by the transfer module. However, no aspheric surfaces are required in the non-disposable focusing ocular.

A generally cylindrical molded plastic prism in the objective is used to provide a field of view angled with respect to the optical axis of the probe. The prism is a unitary solid element. An inclined distal end of the prism is directly juxtaposed to the rear surface of a planar glass window element at the distal end of the probe. Light entering the glass window normal to its surface enters the prism through a first angled end, reflects internally at two reflecting surfaces formed by recesses in the prism, and exits the prism directly along the optical axis of the probe. The refractive index of the plastic of the prism and the angle at which the light rays meet the plastic/air interface of at least one of the reflecting surfaces are such that reflection occurs by total internal reflection within the prism. Accordingly, no more than a single reflecting surface of the prism requires a reflective coating, providing a further economy. The components of the objective, apart from the prism, are identical in several embodiments of the probe having differing viewing angles.

The overall design of the endoscope of the invention thus provides the advantage that the only glass elements employed in the disposable probe are the window element at the distal end of the probe, a plano surfaced window at the proximal end of the transfer module, and the plano surfaced glass rods of the transfer module. These elements are all relatively economical to manufacture. The objective contains the window element, one prism, and three lenses (two of which are identical) while the transfer module only includes two types of lens elements. Each of the lenses in the probe is molded of plastic and accordingly is relatively inexpensive in quantity. The lenses of the disposable probe and the prism may be molded of glass instead of plastic; these alternatives are anticipated to become increasingly attractive as glass molding technology matures.

The non-disposable focusing ocular contains six glass lenses, each including only spherical surfaces. The use of glass elements in the focusing ocular lends durability, and the cost of these glass elements is not significant to the overall cost effectiveness of the endoscope of the invention.

Other objects and advantages of the present invention will become apparent from the following description of the preferred embodiment taken in conjunction with the accompanying drawings wherein like parts in each of the several figures are identified by the same reference characters.

BRIEF DESCRIPTION OF THE DRAWINGS

FIG. 1 is an exploded side view of an endoscopic imaging system according to the present invention;

FIG. 2 is a side view of the optical components of the disposable probe and non-disposable ocular of the endoscope of the present invention;

DESCRIPTION OF THE PREFERRED EMBODIMENTS

Figure 3:
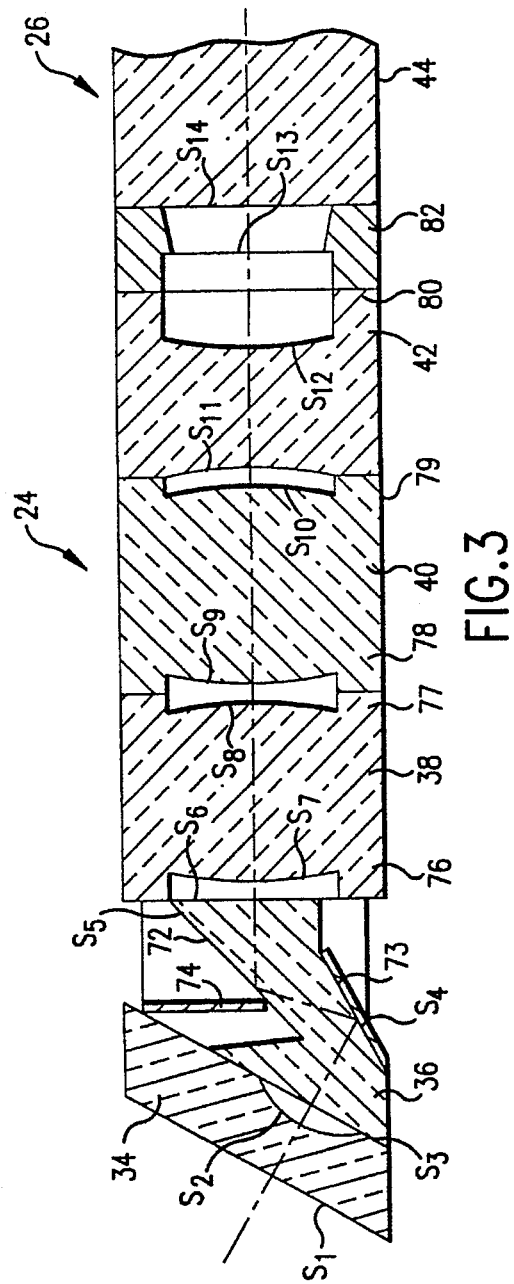
FIG. 3 is a view in longitudinal section of the objective assembly of the disposable probe of the endoscope of the present invention.

FIG. 1 is an exploded view of the principal components of a complete endoscope assembly according to the invention. The disposable probe 10 of the endoscope includes an elongated probe section 12 and a termination 14. The termination 14 comprises a male member 16 received in a recess formed in the body of a non-disposable focusing ocular 20 of the endoscope. The male member 16 may be releasably coupled to the body of the ocular 20 in generally conventional fashion. The art is aware of suitable focusing mechanisms for the ocular 20. The ocular 20 in turn is mated with a video camera 22 or other image forming device in a generally conventional manner well understood by those of skill in the art. As discussed in detail below, the endoscope of the present invention is preferably used in conjunction with a video camera 22 including a so-called "CCD" imaging element and spectral and spatial filter elements.

FIG. 2 is a side view of the complete optical system of the endoscope according to the invention. The external shapes of the termination 14 and ocular 20 are shown in phantom to clarify the relation of these sections of the complete endoscope, but this is not a limitation on the probe of the present invention. The disposable probe 10 comprises an objective group 24 and a transfer module assembly 26. Transfer module assembly 26 comprises three essentially identical relay modules 28, 30 and 32. The relay modules can be multiplied as needed to obtain the desired total probe length; preferably, an odd number of the relay modules is employed to insure that the image is not inverted at the proximal end of probe 10.

As can be seen in FIG. 2, the objective comprises an end window element 34, a prism 36, and three lenses 38, 40 and 42. The structure of the objective 24 is discussed in detail below in connection with FIG. 3. Only the end window element 34 is glass; the prism 36 and the lenses 38, 40 and 42 are all molded of plastic, greatly reducing the overall cost of the disposable probe 10.

In the example of the endoscope of the invention shown in FIG. 2 and discussed throughout this specification, the three relay modules 28, 30 and 32 making up the transfer module assembly 26 together comprise seven plano ended glass rods 44, 45, 46, 47, 48, 49 and 50. Six doublets, each comprising molded plastic lenses 52 and 53, are disposed between each pair of glass rods 44–50. The respective positions of lenses 52 and 53 are reversed where they appear in alternating positions along the transfer module assembly. The transfer module assembly 26 is terminated by an optical window 56 disposed at its proximal end, and is described in detail below in connection with FIG. 4.

The focusing ocular 20 comprises a window 58 designed to be disposed in close proximity to but not touching window 56. Ocular 20 comprises a first glass doublet, comprising elements 59 and 60, which is axially movable to focus the image, a second doublet comprising glass elements 62 and 64, and a third doublet including elements 66 and 68. The focusing ocular 20 is described in detail below in connection with FIG. 5.

Having now briefly identified the components of the disposable endoscope of the invention, a discussion will now be provided of the structure and functions of each. Subsequently the detailed optical specifications of each of the elements will be presented.

As discussed above, the endoscope of the present invention comprises a disposable probe 10, the probe 10 including a distal objective 24 for forming an image and a transfer module assembly 26 for transferring the image from the distal end of the probe to the proximal end of the probe, and a focusing ocular group 20 for presenting this image to a video camera 22 or equivalent device for providing a visible image. The prior art has invariably (so far as known to the present inventor) attempted to provide self-correcting endoscope probes; that is, the prior art has attempted to provide endoscope probes forming an image including no residual aberration to be corrected by the focusing ocular. The prior art suggests that one element of an endoscope probe may be designed to correct optically for aberration introduced by another group of the probe. For example, in Yamashita et al U.S. Pat. No. 4,165,917 the astigmatism of the objective is corrected by the relay lens group (i.e. the transfer module), whereby the image presented to the ocular is fully corrected. However, as mentioned above, the art does not suggest that aberrations introduced by the probe might usefully be corrected by the ocular.

According to an important feature of the present invention, the image provided by the probe is permitted to include certain aberration to be corrected by the focusing ocular. The aberration in the image provided by the probe is sufficiently severe that if the image were not corrected it would be considered unacceptably distorted. Correction by the ocular of residual aberration in the image formed by the probe permits very substantial simplification of the optical design of the disposable probe of the invention, reducing the cost of the probe such that it is cost-effective for disposability after single patient use. In particular, this has enabled placement of substantially all costly glass elements having curved surfaces in the non-disposable ocular 20, while the disposable probe 10 principally includes molded plastic focusing lenses and plano-ended glass rods.

More specifically, relatively large amounts of field curvature, axial chromatic aberration, and lateral chromatic aberration, as well as astigmatism, exist in the image formed by the disposable probe 10 of the invention, but the image is nearly completely corrected with respect to spherical aberration and coma. The non-disposable ocular 20 comprises optical glass elements eliminating the residual aberration in the image provided by the disposable probe. Of course the ocular 20 must also correct any optical aberration introduced by its own design. The ocular 20 also includes an axially movable glass doublet for focusing the endoscope of the invention. Provision of the focusing mechanism in the non-disposable ocular rather than in the disposable probe further reduces the cost of the probe.

Referring now to the individual elements of the probe of the invention, the individual surfaces through which rays from the object pass are identified herein and in the accompanying drawings and claims, and are specified in Table I below, by individual surfaces numbered $S_1$ to $S_{71}$, reading from the distal tip of the probe to the imaging Surface of a CCD sensor comprised by the video camera 22.

The objective 24 comprises a glass window element 34 at the distal tip of the probe, the prism 36, and three optical elements 38, 40, and 42. The glass window element 34 at the tip of the probe provides satisfactory bio-environmental compatibility. Window element 34 has a planar distal surface $S_1$ and a concave lens surface $S_2$ (see FIG. 3) formed on its inner planar surface for broadening the field of view of the probe. The plano-concave window element 34 is formed of a high index of refraction crown glass providing improved control of the lateral chromatic aberration of the objective. Lateral chromatic aberration introduced by the window 34 is corrected by the use of a high index flint-like optical plastic for the prism 36, which also corrects lateral chromatic aberration introduced by the two elements 38 and 40 immediately following the prism.

An equivalent front window element 34 might be manufactured conveniently with an aspheric inner surface. This can be accomplished by fabricating a glass substrate having a planar outer surface and a spherical concave inner surface. A quantity of suitable optical plastic or resin material is disposed in the concavity, and pressed against an aspheric mold member under suitable conditions of temperature and pressure to mold the aspheric surface. Such processes are generally known to the art.

The prism 36 of the present invention is a unitary injection molded member made of a moderately high refractive index material such as NAS (an acrylic/polystyrene copolymer). As noted above, as glass molding technology matures, it may become feasible to mold the prism of glass. The prism has two internal reflecting surfaces $S_4$ and $S_5$ so that the image retains its proper image "hand". In the embodiment shown of prism 36, whereby the field of view is inclined at 25° to the optical axis of the probe 10, the refractive index of the material of the prism 36 and the angles of the reflecting surfaces $S_4$ and $S_5$ can be chosen such that reflection takes place at surface $S_5$ according to total internal reflection. Accordingly, only reflecting surface $S_4$ need be coated with a layer 73 of reflective material, further simplifying and reducing the cost of the manufacturing operation.

The prism 36 is generally cylindrical, having a distal planar surface $S_3$ juxtaposed to glass window element 34 at the tip of the probe 10. Surface $S_3$ and window element 34 are inclined at an angle to the optical axis of the prism normal to the center of the field of view of the probe. The proximal planar surface $S_6$ of the prism 36 is orthogonal to the optical axis of the probe. In this way, both the entry and exit surfaces of the prism 36 are perpendicular to rays along the optical axis, for control of optical aberration.

Three molded plastic lenses 38, 40, and 42 follow the prism in the objective group 24. Lenses 38 and 40 are physically identical, but their relative orientations are reversed. The third lens 42 is unique. The two identical lens elements 38 and 40 each include one aspheric surface (these being identified as surfaces $S_8$ and $S_9$ in FIG. 3) and one spherical surface ($S_7$ and $S_{10}$). This arrangement provides improved control of spherical aberration and astigmatism. Aberration control by the aspheric surfaces $S_8$ and $S_9$ is necessary due to the effective location of the aperture stop in the center of the fore-oblique prism 36; some rays pass through the two central elements far from the optical axis.

The final element of the objective, lens 42, is also injection molded, from a flint-like optical plastic material. Use of the flint-like material permits this element to compensate for much of the axial and lateral chromatic aberration introduced by the preceding elements. The choice of an uncemented final element 42 permits its front surface $S_{11}$ to be curved independently of element 40, compensating for astigmatism introduced by the preceding elements.

The elements of the objective are spaced from one another by air gaps. Precise control of the lengths of the air gaps is provided by spacer members 76, 77, 78, 79 and 80 integrally molded around the peripheries of the optical surfaces. These integral spacers eliminate the need for separate small components, avoiding the cost of their fabrication and assembly. A further spacer 82 is provided between the third element 42 of the objective and the first glass rod 44 of the transfer module assembly 26. The inner periphery of spacer 82 is the field stop, identified as surface $S_{13}$. The field stop 82 is thus physically located between the proximal element 42 of the objective and the transfer module assembly 26.

As described above, in a typical endoscope according to the present invention the transfer module assembly 26 may be considered to comprise three substantially identical relay modules 28, 30 and 32. The transfer module assembly is shown in further detail in FIG. 4. The number of relay modules in the transfer module assembly can be extended more or less indefinitely, although odd numbers of relay modules are typically used to preserve image orientation.

The relay modules 28, 30 and 32 each comprise an entry glass rod, a first doublet, an intermediate glass rod, a second doublet, and an exit rod. The exit rod of one relay module and the entry rod of the succeeding rod are preferably configured as a single rod, as shown. As discussed in detail below in connection with FIG. 13, intermediate images are formed within the glass rods extending between the relay modules. By thus forming the intermediate images within the rods, rather than at their surfaces or in air gaps between the rods, the possibility is eliminated that a scratch or other defect on a rod end surface might interfere with formation of a suitable visible image.

Figure 4:
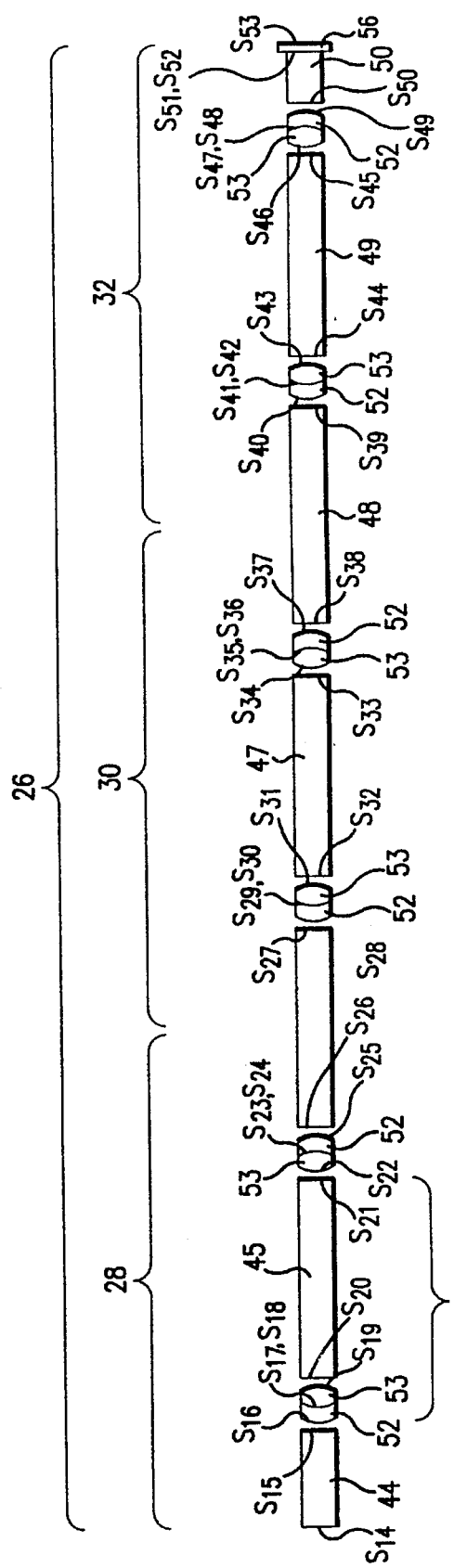
FIG. 4 is a side view of one of the transfer modules of the transfer module assembly of the probe of the endoscope of the present invention.

The transfer module assembly 26 may also usefully be considered to comprise a number of relay subgroups 33, each comprising a doublet and an intermediate rod, juxtaposed to one another to make up the bulk of the length of the transfer module assembly. As thus defined, two relay subgroups 33 make up a relay module; the complete transfer module assembly shown in FIG. 4 is made up of five identical subgroups 33, a relatively short glass entry rod 44, and an exit subgroup including a sixth identical doublet and a relatively short exit glass rod 50.

Each of the glass rods 44, 45, 46, 47, 48, 49, and 50 of the transfer module assembly is plano-ended, reducing cost. Further, rods 45–49 are of identical length, again reducing cost. The surfaces of rods 44–50 are identified in FIG. 4 corresponding to the listings of the rods in Table I below. Thus, the entry surface of the first glass rod 44 of the relay module 28 is identified as $S_{14}$.

The relay modules 28, 30 and 32 each further comprise two doublets each including two molded plastic lenses 52 and 53. Lenses 52 and 53 are thus used twice in each relay module, with their orientation with respect to one another in each doublet being reversed according to the respective position of the doublet within the relay module, as shown in FIG. 4. As in the case of elements 38, 40 and 42 of the objective (FIG. 3), the molded plastic lenses 52 and 53 of each doublet preferably include integrally molded spacers (not shown) defining the air gaps between lenses 52 and 53 and the adjoining glass rods, to further simplify assembly of the probe and reduce its cost.

One surface of element 53 of each of the doublets is aspheric, e.g., surface $S_{19}$ of the first occurring element 53 and surface $S_{22}$ of the second occurring element 53. Aspheric surfaces are used in each element 53 to substantially reduce the spherical aberration. Residual field curvature and axial and lateral chromatic aberration are eliminated by the optics of the ocular, as discussed previously.

Ideally, the two elements 52 and 53 of each of the doublets are cemented together to minimize alignment sensitivity and light loss. However, this is not necessarily required; use of air-spaced doublets will further reduce the instrument cost.

An alternative to the use of an aspheric surface on one of the two elements 52 and 53 of the doublets of the transfer module assembly is to replace each of the doublets with a three-element system in which aspheric surfaces can be avoided. As lenses having aspheric surfaces cost no more to mold than spherical lenses, the embodiment shown is preferred.

The principal advantage of the design shown is that the plano-ended glass rods can be manufactured very readily, since no curved glass surfaces need to be polished. Employing only two types of molded plastic lens allows the lenses to be manufactured relatively inexpensively in high quantity by injection molding. As noted above, the lenses 52 and 53 might equivalently be molded of glass rather than plastic.

As stated above, seven plano-ended glass rods 44, 45, 46, 47, 48, 49 and 50 are used in the exemplary transfer module assembly shown in the drawings. Rods 45, 46, 47, 48, and 49 are identical and their length is kept to a minimum to reduce the chance of breakage, a critical issue in arthroscopic and similar applications where physical stress on the device may be substantial. Rods 44 and 50 are of different lengths in order to accommodate the objective and the ocular window geometries. The chance of breakage is further reduced by provision of plastic spacers (not shown) integrally molded on the end of the intervening lenses 52 and 53, since these spacers absorb much of the compressive stress encountered upon bending of the probe of an endoscope. Prior art designs employing metal spacers between glass lenses force the compressive stresses to be absorbed by the fragile glass components. Alternative embodiments of this invention reduce the rod lengths to further minimize the chance of breakage by dividing rods 45, 46, 47, 48 and 49 into two shorter identical rods with an intervening plastic spacer.

Figure 5:
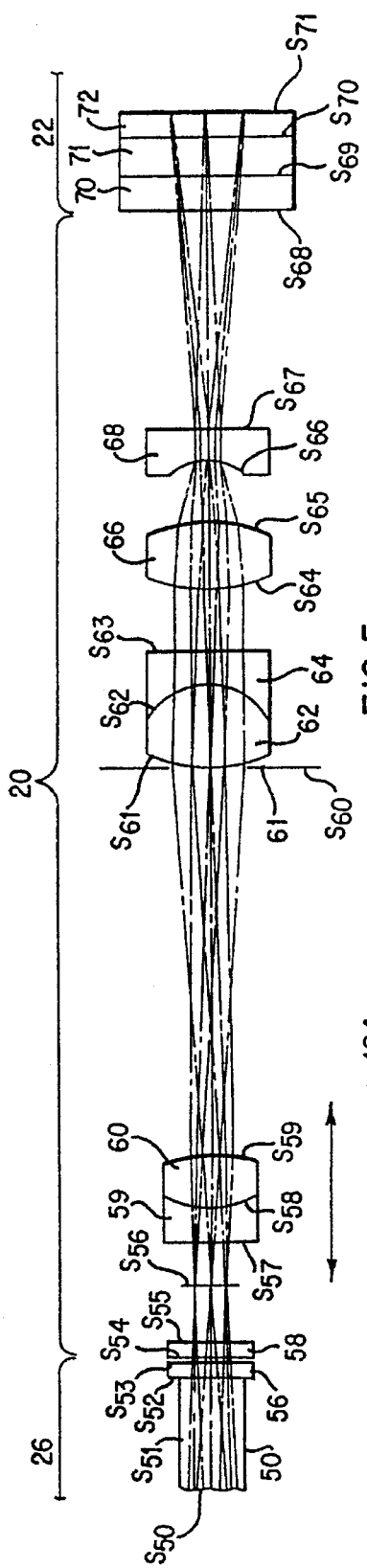
FIG. 5 is an optical schematic diagram of the optical components of the non-disposable focusing ocular of the endoscope of the present invention.

Referring now to FIG. 5, the ocular optical design comprises an axially movable cemented focusing doublet comprising elements 59 and 60 near an intermediate image location denoted by object surface $S_{56}$. Focusing doublet 59, 60 bends the telecentric chief ray down toward the aperture of the following elements. Doublet 59, 60 also provides correction of lateral chromatic aberration. The ocular 20 also comprises a second cemented doublet, comprising elements 62 and 64, and a third air-spaced doublet comprising elements 66 and 68. The second cemented doublet comprising elements 62 and 64 could also be designed as an air-spaced doublet, but the cemented form is preferred since the manufacturing tolerances thereon are more forgiving. The second cemented doublet comprising elements 62 and 64 provides most of the image forming power of the system, and provides substantial correction of the axial chromatic aberration of the overall system.

The air-spaced doublet comprising elements 66 and 68 uses two glass types to permit correction of most of the lateral chromatic aberration of the overall system. The airspace allows the juxtaposed surfaces $S_{65}$ and $S_{66}$ of elements 66 and 68 to be strongly curved to correct astigmatism introduced by the remainder of the ocular group and to correct residual astigmatism and field curvature in the image received from the disposable probe 10.

As discussed above, the ocular 20 provides focus adjustment for changes in object distance by axial displacement of the focusing doublet 59, 60. Focus adjustment is effective for object distances from infinity to the outer surface of the objective window 34 with very little loss in image quality. The use of weakly powered elements for focusing makes both image location and quality reasonably insensitive to radial displacement of the element during focus adjustment. Field curvature remaining in the image received from the transfer module assembly 26 is corrected by convex surface $S_{66}$ formed on element 68 of the ocular 20.

FIG. 5 also shows for completeness three plano-surfaced window elements 70, 71 and 72 provided as part of the video camera 22 with which the endoscope of the invention is preferably utilized. 21 Window 72 protects the CCD imaging element of the video camera 22. Window 71 is an infrared filter, that is, a spectral filter removing infrared components from the imaged light. Substantially all CCD video cameras sold for endoscopic imaging purposes include suitable elements 71 and 72. The third window element shown is a spatial filter 70 provided in certain video cameras sold for endoscopic imaging purposes by the Sony Corporation of Japan. Such spatial filters prevent aliasing of the image formed by the CCD element, and their use is accordingly preferred. However, the endoscope of the invention is useful with CCD video cameras not including such spatial filters 70; accordingly, the detailed optical specifications given below of the endoscope of the invention need not vary in dependence on the presence or absence of spatial filter 70.

FIGS. 6–10 provide details of the prism 36. Window element 34 is also shown in phantom in FIG. 10 for clarity. As can be seen, the prism 36 is a generally cylindrical solid member, having a first recess 90 formed in its "top" (in the orientation shown) and a second recess 92 formed in its "lower" surface. The innermost surface $S_5$ of recess 90 is planar, as is the innermost surface $S_4$ of recess 92. Rays entering the prism 36 at a distal inclined surface $S_3$ reflect in sequence from surfaces $S_4$ and $S_5$ and exit the prism 36 through proximal planar end surface $S_6$. Line 100 indicates the axis of the field of view. Lines 101 and 102 indicate the path in the prism of the ray entering the prism along the axis of the field of view 100. The ray exits the prism along line 103, that is, along the optical axis of the probe. The surface $S_3$ at which the prism 36 is juxtaposed to the window 34 at the tip of the disposable probe of the endoscope according to the invention is normal to the axis of the field of view of the endoscope defined by line 100. Rays from the center of the field of view are thus normal to the oblique entry surface $S_3$ of the prism 36 and exit the prism orthogonal to the proximal exit surface $S_6$, in order to reduce aberration.

The detailed specifications of the prism vary with the desired viewing angle, that is, with the desired angle made between the axis 100 of the field of view and the optical axis 103 of the probe. In the embodiment shown in FIGS. 6 through 10 this angle is 25°. Accordingly, angle A, between the distal surface $S_3$ and the optical axis, is 65°. Angle B, the angle between the first reflecting surface $S_4$ and the optical axis, is 21.5°, and angle C, between the second reflecting surface $S_5$ and the rear face of the prism 36, is 56°. Surface $S_5$ thus is oriented at an angle of 34° to the optical axis. It is within the scope of the invention to provide prisms having different viewing angles which may, in some cases, exceed 9°, providing a retrograde field of view. Further, it is also within the scope of the invention to replace the prism 36 shown by a single cylindrical element in order to form an image of a field of view directly centered on the optical axis of the probe. No modification to the optical design of the remainder of the objective, the transfer module assembly, or the ocular is required to do so.

Figure 9:
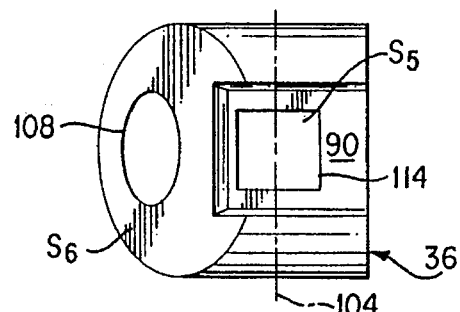
FIG. 9 is a top view in plan of the prism.
Figure 8:
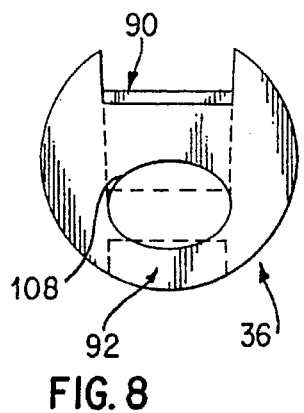
FIG. 8 is a distal end view of the prism.
Figure 7:
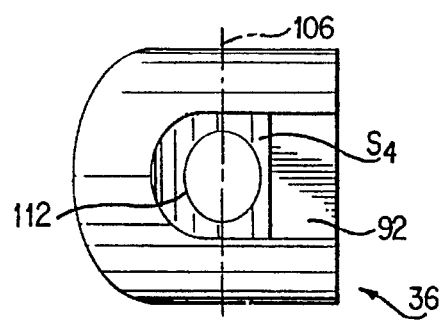
FIG. 7 is a view in plan of the prism from its underside.

It will be apparent by study of FIGS. 7 and 9 that if imaginary longitudinal lines bisecting the reflecting surfaces $S_4$ and $S_5$ are drawn they will intersect the optical axis, i.e., that the reflecting surfaces are longitudinally centered on the optical axis. Similarly, transverse, lines 104 and 106 drawn on each of the reflecting surfaces $S_5$ and $S_4$, respectively, orthogonal to these longitudinal lines are parallel to one another and accordingly orthogonal to the optical axis.

In the 25° embodiment of the prism of the invention shown in FIGS. 6 through 10, it is possible to select the index of refraction of the material of the prism 36 with respect to the angle of incidence of the rays on the second reflecting surface $S_5$ such that reflection of the rays takes place entirely within the prism, due to total internal reflection, and so that no reflective coating is required on surface $S_5$, simplifying the manufacture of the prism.

The preferred material of the prism is injection molded plastic. A suitable material known as NAS is a copolymer of 70% polystyrene and 30% acrylic. A particularly suitable choice is NAS30 material, sold by Polysar, Inc., having an index of refraction of 1.564 and a dispersion of 35.0. (Throughout this specification and the appended claims, all values for indices of refraction refer to the index of refraction measured with respect to the "D-line" in the sodium spectrum, as is conventional.)

A reflective coating 73, e.g., of aluminum, is required on surface $S_4$. Preferably the end surfaces $S_3$ and $S_6$ are provided with an anti-reflection coating to insure maximum transmission of the light being gathered. The second reflective surface $S_5$ should be left optically clear for total internal reflection.

In some embodiments of the invention it may be desired to provide an opaque baffle 74 within the recess 90 to prevent stray light from entering the optical path through surface $S_5$. The lower extremity of baffle 74 must be spaced from the reflecting surface $S_5$.

Figure 10:
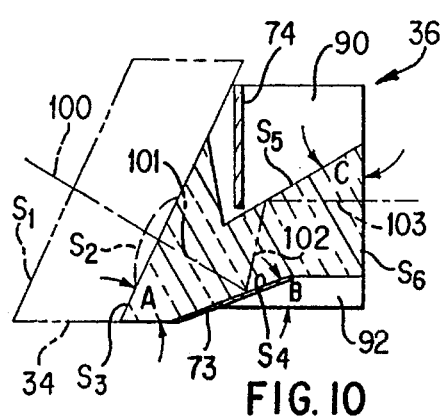
FIG. 10 is a view in section of the prism taken along the line 10—10 of FIG. 6.
Figure 6:
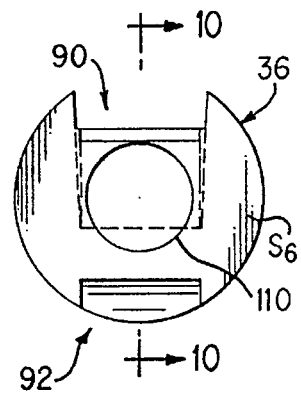
FIG. 6 is a proximal end view of the prism of the disposable probe of the endoscope of the present invention.

As shown in FIG. 10 and also in FIG. 3, a concave lens surface $S_2$ is formed in the glass window element 34 to which the front surface $S_3$ of the prism 36 is juxtaposed. This concave lens surface $S_2$ is centered about the axis of the field of view 100. The function of this concave lens surface $S_2$ is to collect light from a broad field of view.

In order that light gathered by lens surface $S_2$ can be efficiently transmitted by the prism, it is important that a region 108 (FIG. 9) on surface $S_3$ remain optically clear. In the particular implementation of the endoscope of the invention specified by Table I below (in which each of the elements of the probe 10 are of 3.5 mm outside diameter), this region 108 is approximately 1.5 mm in diameter. Similarly, the rear surface $S_6$ (FIG. 6) of the prism should have a clear aperture 110 at least 1.525 mm in diameter. A central section 112 (FIG. 7) of first reflecting surface $S_4$, approximately 1.27 by 1.00 mm, similarly must be clear prior to application of reflective coating 73, and the second reflecting surface $S_5$ (FIG. 9) should include a rectangular clear aperture 114 typically measuring 1.27 by 0.90 min.

Figure 11:
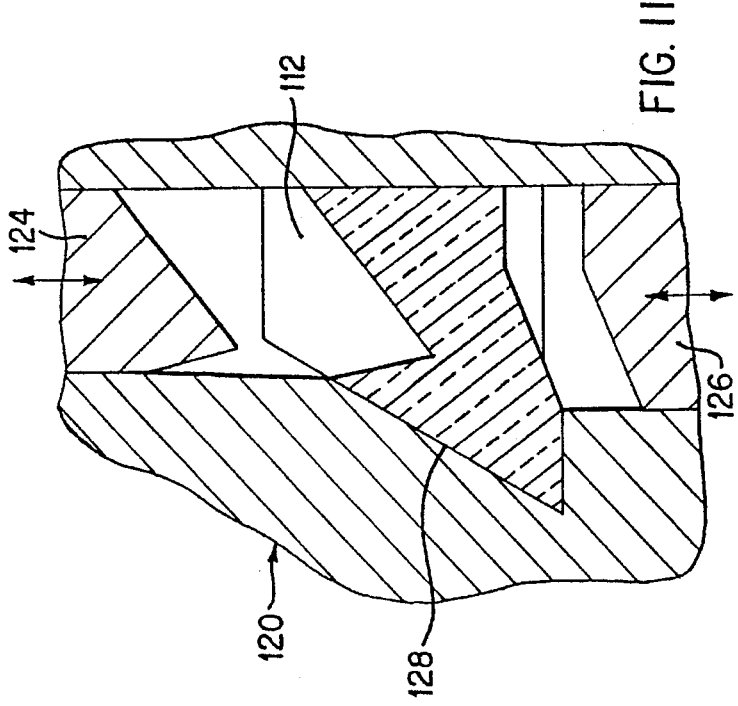
FIG. 11 is a view in section of a mold suitable for manufacture of the prism.

Preferably the prism 36 is manufactured by injection molding. A suitable mold 120 is shown in FIG. 11. The mold 120 includes a mold cavity 112 generally conforming to the cylindrical outline of the prism, having one end orthogonal to the cylindrical axis and one oblique end, conforming to the surfaces $S_6$ and $S_3$ of the prism, respectively. The mold 120 includes two opposed slide members 124 and 126 to be controllably inserted into and withdrawn from the mold cavity 112. The slide members 124 and 126 have distal tips corresponding in shape to the desired recesses 90 and 92 in the prism. Manufacture of the prism simply involves the steps of inserting the slide members 124 and 126 into the mold cavity, injecting the appropriate Polysar NAS30 acrylic material, allowing it to cool and harden, withdrawing the slide members 124 and 126 from the mold cavity 112 to the positions shown in FIG. 11, and withdrawing the hardened prism precursor 128 from the mold cavity. The first reflecting surface $S_4$ is then coated with suitable reflective material, and the remaining critical surfaces are coated with a suitable anti-reflection coating.

The optical parameters of the other elements of a particular implementation of the endoscope will now be summarized, after which there is provided Table I detailing each of the critical optical parameters of this implementation of the invention.

In the following, optical components having flat or spherical surfaces are specified by definition of the radii of their ends, the index of refraction and the dispersion of their materials, and by their thickness along the optical axis. Aspheric surfaces are defined in this specification and the appended claims by the values needed to complete the following equation:

$$z = \frac{ch^2}{1 + [1 - (l + k)c^2h^2]^{1/2}} + Ah^4 + Bh^6 + Ch^8 + Dh^{10}$$

wherein:
A, B, C, and D are constants;
k is the conic constant of the surface;
c is the basic curvature of the surface, such that c=1/R in the case where k=A=B=C=D=0, and the equation defines a spherical surface of radius R; and
z is the sagitta, that is, the distance between a plane tangent to the aspheric surface at the optical axis and all points P (h,z) on the surface a radial distance h measured orthogonal to the optical axis.

Figure 12:
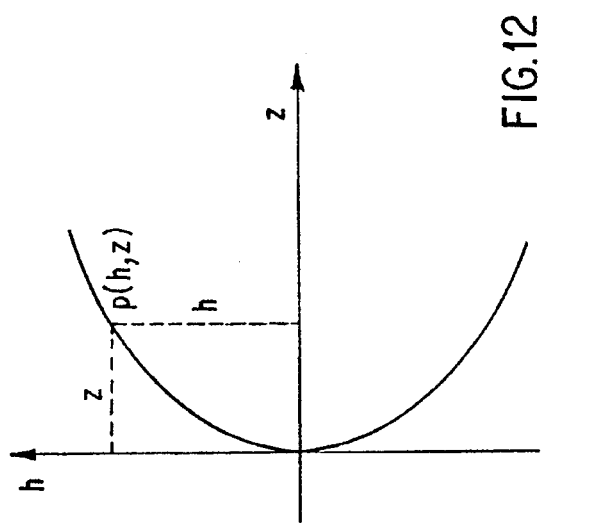
FIG. 12 is a plot of surface sagitta versus radius specifying the terminology employed to define the aspheric surfaces of lenses in the probe of the endoscope of the present invention.

FIG. 12 explains the values of the variables z and h appearing in this equation. Points P (h,z) define the aspheric surface, appearing in two dimensions as a parabola. All points P (h,z) lie on a circle of radius h (or "semi-diameter", in optical parlance) on the aspheric surface, where z is the sagitta, that is, is the length of a normal from the plane tangent to the spherical surface at the optical axis to the circle.

As indicated by the equation above, the curvature of an aspheric surface is defined by four constants A, B, C and D, the conic constant k, and c, the basic curvature of the surface. Specifically, curvature c=1/R, where R is the radius of the spherical surface defined by the equation given above in the special case where the conic constant k and constants A, B, C and D are all set equal to zero.

This method of defining an aspheric surface is an industry standard and familiar to those skilled in the art.

Accordingly, the aspheric surfaces of the exemplary implementation of the optical system of the endoscope of the invention are adequately described in Table I by listing values for A, B, C, D, c, and k. The curvature c is specified by giving the inverse value of the base radius R. Similarly, in the claims appended to this specification, aspheric surfaces are defined by provision of these six values, and reference is to be made to the equation above for their definition.

As is conventional in the optical art, the spherical elements of an exemplary implementation of the endoscope of the invention are specified in Table I by the radii of their surfaces (a negative sign indicating the center of the surface is disposed more closely to the distal tip of the probe than is the surface, as is conventional), the thickness of the element, and the index of refraction and dispersion of the material. The surfaces $S_1$–$S_{71}$ appearing in Table I are specifically identified in FIGS. 3–10. Table T further includes specification of the suitable materials for each of the elements.

Thus, for example, the window 34 at the tip of the probe is shown by Table I to be formed of type LAF2 optical glass having index of refraction 1.744 and dispersion 44.72. Its outer surface $S_1$ is planar (i.e., of infinite radius) and its inner surface $S_2$ concave and of 1.1765 mm radiuses. The central thickness of window 34 measured along the center of the field of view is 0.762 mm. Surface $S_2$ is centered on axis 100, the center of the field of view of the system. Axis 100 is at 25° to the optical axis of the probe in this implementation of the invention. The outer planar surface $S_1$ of the glass window 34 is orthogonal to the axis 100.

The next element in the objective section 24 of the probe 10 is the prism, as discussed above in detail. As there indicated, the prism is molded of Polysar NAS30 plastic, having a index of refraction of 1.564 and dispersion of 35.0. The front surface $S_3$ at which the prism 36 is juxtaposed to the window 34 is inclined at an angle of 25° to the optical axis; its first reflective surface $S_4$, having a reflective coating 73 thereon, is inclined at angle B of 21.5° to the optical axis. The inclination of surface $S_4$ is specified in Table I by the angle of 43.5° between $S_4$ and the entry surface $S_3$ of the prism 36. Second reflecting surface $S_5$ of the prism 36 is inclined at 34° to the optical axis; this relation is specified in Table I by the 56° angle, angle C, between $S_5$ and the proximal planar end $S_6$ of the prism 36.

Lenses 38 and 40 have identical surface curvatures, but are reversed with respect to one another. Thus the surface $S_7$ of lens 38 disposed toward the prism, and surface $S_{10}$ of lens 40 disposed toward the third lens 42 of the objective group have the same 3.302 mm convex radius, while their facing surfaces $S_8$ and $S_9$ are convex aspheric, having specifications which will be found in the Table. Lenses 38 and 40 are molded of polymethylmethacrylate ("PMMA") plastic, for example, Rohm and Haas Company V920 acrylic plastic having an index of refraction of 1.492 and dispersion of 57.4. The central thickness of lenses 38 and 40 is 2.286 min. Other grades of acrylic molding resins may be satisfactory.

The third lens 42 of the objective group is formed of Polysar NAS30 plastic, again having an index of refraction of 1.564 and dispersion of 35.0. Its concave surface $S_{11}$ facing toward the prism is of 7.126 mm radius and its surface $S_{12}$ disposed toward the transfer module is also concave, with a radius of 4.942 mm.

As shown in FIG. 3, each of lens 38, 40 and 42 are formed to comprise integral spacers, so that their surfaces are spaced by air gaps the lengths of which are specified in Table I.

The next optical element in the endoscope of the invention is the entrance rod 44 of the transfer module assembly 26. Rod 44 is 12.70 mm long, plano-ended, and made of BASF2 glass, having an index of refraction of 1.6644 and a dispersion of 35.83. Entrance rod 44 is spaced from the third lens 42 of the objective group by a spacer 82. The inside surface of spacer 82 provides the field stop for the system, appearing as $S_{13}$ in Table I. The inside diameter of the field stop is 2.05 mm. The axial spacing between the proximal surface $S_{12}$ of lens 42 and the distal surface $S_{14}$ of the first glass rod 44 of the transfer module assembly 26 is given in Table I and totals 2.684 mm.

As noted, according to an important aspect of the invention, each of the five glass rods 45, 46, 47, 48 and 49 of the relay modules 28, 30 and 32 of transfer module assembly 26 are identical. Each of the five rods 45–49 has a central length of 28.575 mm, has planar end surfaces of infinite radius and is also formed of BASF2 optical glass. The fact that these rods 45–49 are all identical and that all of the rods 44–50 of the transfer module assembly have planar end surfaces contributes materially to making the endoscope of the invention sufficiently inexpensive that it can be cost effective for single patient, disposable use.

As discussed above, FIG. 4 shows the transfer module assembly 26 which comprises seven glass rods 44, 45, 46, 47, 48, 49 and 50, and twelve lenses 52 and 53, arranged as six doublets. The transfer module assembly 26 thus comprises three substantially similar relay modules, 28, 30 and 32, each including an entry rod, a first doublet, an intermediate rod, a second doublet, and an exit rod. The exit rod of one relay module and the entry rod of the next may be configured as a single continuous member, as shown, to reduce the number of parts and of optical surfaces. The transfer module assembly as shown may also be considered to comprise six relay subgroups 33, each consisting of a doublet and a plano-ended glass rod, together with entry rod 44.

As discussed above, the elements 52 and 53 of the first doublet of each relay module are optically identical to the elements 52 and 53 respectively of the second doublet, but are physically reversed. The distal entry surface $S_{16}$ of the first element 52 of the first doublet is thus optically identical to the proximal exit surface $S_{25}$ of the second element 52 of the second doublet. As specified in Table I, these surfaces are convex with radius 9.233 min. The thickness of element 52 along the optical axis is 1.778 mm and the radius of the opposing surface, e.g., surface $S_{17}$ of the first element 52, is 4.335 min. Elements 52 are molded from Polysar, Inc. NAS30 plastic which as above has an index of refraction of 1.564 and a dispersion of 35.0.

The second element 53 of each doublet is similarly identical. The elements 53 each contact the corresponding elements 52, e.g., at surface S18 for the first element 53, which accordingly is convex with a radius of 4.335 mm. The other surfaces of each of these elements, e.g. $S_{19}$ for the first element 53, are aspheric having characteristics defined by Table I. Elements 53 have an axial thickness of 2.286 mm and are formed of polymethylmethacrylate (PMMA) plastic, e.g., Rohm and Haas Company V920 acrylic plastic, having as mentioned above an index of refraction of 1.492 and dispersion of 57.4.

The last rod element 50 in the transfer module assembly 26 is also formed of BASF2 glass, is plano-ended and is 6.35 mm long.

The transfer module assembly is terminated by a window 56 having surfaces $S_{52}$ and $S_{53}$. As shown in Table I these surfaces are both optically flat, specified as of infinite radius. The window 56 is 1.000 mm thick and is formed of type BK7 optical glass, having index of refraction 1.516 and dispersion 64.17.

The focusing ocular meets the transfer module at a generally similar window 58 having surfaces $S_{54}$ and S55. The radii of these two planar surfaces are infinite. Window 58 is also 1 mm thick and of type BK7 glass.

As shown in Table I, the entry surface S57 of the distal element 59 of the movable focusing doublet comprising lenses 59 and 60 is of infinite radius and its exit surface $S_{58}$ is concave of 6.573 mm radius. The central thickness of element 59 is 2.032 mm. Element 59 is formed of type SK5 optical glass having index of refraction 1.589 and dispersion 61.27.

The second lens 60 of the focusing doublet is cemented to the first lens 59. Accordingly a single entry in Table I is provided for surface $S_{58}$, specifying the mating surfaces of elements 59 and 60. The second element 60 of the focusing doublet is formed of type F8 optical glass of index of refraction 1.595 and dispersion 39.18, is 2.681 mm thick, and has an exit surface $S_{59}$ of 14.126 mm radius. In the preferred embodiment the focusing doublet comprising elements 59 and 60 is provided with axial motion of at least about 2.54 mm to enable focusing of the endoscope from the front surface of the window 34 to infinity. An aperture stop 61 is provided between the doublet consisting of lenses 59 and 60 and the doublet consisting of lenses 62 and 64. The axial location of aperture stop 61 is specified by $S_{60}$ in Table I.

The first element 62 of the second doublet of the ocular as shown in Table I has an convex entry surface $S_{61}$ of 9.824 mm radius and exit surface $S_{62}$ which is convex with a radius of 3.81 mm. This lens has a central thickness of 4.572 mm and is formed of type SK16 optical glass having a index of refraction of 1.620 and dispersion of 60.33.

As elements 62 and 64 of the second doublet are cemented to one another, a single entry for surface $S_{62}$ defines their mating surfaces. Exit surface $S_{63}$ of lens 64 is of infinite radius, and its thickness is 2.032 min. The material of lens 64 is type LAF2 optical glass having index of refraction of 1.744 and dispersion of 44.72.

The second doublet is spaced by an air gap given in Table I from a third airspaced doublet consisting of a first lens 66 and a second lens 68. Entry surface $S_{64}$ of the first lens 66 is convex of radius 8.604 mm and exit surface $S_{65}$ is convex of radius 8.604 mm. The central thickness of this lens 66 is 3.81 mm. Lens 66 is formed of type SK5 optical glass having an index of refraction of 1.589 and dispersion of 61.27.

The second lens 68 of the third airspaced doublet has a entry surface $S_{66}$, concave with a radius of 2.908 man. Its exit surface $S_{67}$ is of infinite radius and its central thickness is 2,032 mm. Element 67 is formed of type SF11 optical glass having an index of refraction 1.784 and dispersion equal to 25.76.

The last three elements in the system are filters and windows provided in the preferred CCD video camera. As discussed above, element 70 is a spatial filter provided in certain preferred Sony video cameras, element 71 is a spectral filter removing infrared radiation from the imaged light, and element 72 is a protective window. Table I provides the critical specifications of elements 70–72. Surface $S_{71}$ is the active surface of the CCD imaging element of the video camera 22. As noted above, the presence of elements 70–72 is not required.

Table I following summarizes the optical specifications just given, and additionally provides the specifications of the aspheric surfaces molded on the various plastic elements. Table I also provides all relevant airspaces and other information not specifically given above. Table I also reflects the fact that a drop of distilled water may usefully be placed between the windows 56 and 58 of the probe and ocular, respectively, to exclude air and prevent fogging due to condensation. Table I thus provides a complete optical prescription for a disposable endoscope; from this information, one of skill in the art would have no difficulty in constructing an endoscope according to the present invention.

TABLE I

| Sn | Radius (mm) or Aspheric Terms or (Tilt Angle) | Thickness (mm) | Medium | Refractive Index (Nd) | Dispersion (Vd) | Element | Assembly |
|---|---|---|---|---|---|---|---|
| 1 | INFINITY | 0.762000 | LAF2 | 1.74400 | 44.72 | window/ele 1 (34) | Objective Group (24) |
| 2 | 1.17650 | 0.270000 | AIR | | | | |
| 3 | INFINITY | 1.651000 | NAS30 | 1.56400 | 35.00 | prism (36) | |
| 4 | INFINITY (−43.50) | −1.524000 | REFL (NAS30) | | | | |
| 5 | INFINITY (+56.00) | 1.778000 | REFL (NAS30) | | | | |
| 6 | INFINITY | 0.127000 | AIR | | | | |
| 7 | 3.30200 | 2.286000 | PMMA | 1.49200 | 57.40 | lens (38) | |
| 8 | c = −0.249431<br>k = −1.026659<br>A = 0.491000E-02<br>B = 0.133746E-02<br>C = D = 0.0 | 0.356564 | AIR | | | | |
| 9 | c = 0.249431 | 2.286000 | PMMA | 1.49200 | 57.40 | lens (40) | |

TABLE I-continued

| Sn | Radius (mm) or Aspheric Terms or (Tilt Angle) | Thickness (mm) | Medium | Refractive Index (Nd) | Dispersion (Vd) | Element | Assembly |
|---|---|---|---|---|---|---|---|
|  | $k = -1.026659$ |  |  |  |  |  |  |
|  | $A = -0.491000E-02$ |  |  |  |  |  |  |
|  | $B = -0.133746E-02$ |  |  |  |  |  |  |
|  | $C = D = 0.0$ |  |  |  |  |  |  |
| 10 | −3.30200 | 0.241087 | AIR |  |  |  |  |
| 11 | −7.12576 | 1.651000 | NAS30 | 1.56400 | 35.00 | lens (42) |  |
| 12 | 4.94207 | 1.674264 | AIR |  |  |  |  |
| 13 | INFINITY | 1.016000 | AIR |  |  | int. image |  |
| 14 | INFINITY | 12.700000 | BASF2 | 1.66446 | 35.83 | rod (44) | Transfer Module (26) |
| 15 | INFINITY | 0.254000 | AIR |  |  |  |  |
| 16 | 9.23300 | 1.778000 | NAS30 | 1.56400 | 35.00 | lens (52) |  |
| 17 | 4.33469 | 0.000000 | CEMENT/AIR | 1.56000 | 44.00 |  |  |
| 18 | 4.33469 | 2.286000 | PMMA | 1.49200 | 57.40 | lens (53) |  |
| 19 | $c = -0.121238$ | 0.254000 | AIR |  |  |  |  |
|  | $k = -1.317139$ |  |  |  |  |  |  |
|  | $A = -0.269762E-04$ |  |  |  |  |  |  |
|  | $B = 0.681709E-04$ |  |  |  |  |  |  |
|  | $C = D = 0.0$ |  |  |  |  |  |  |
| 20 | INFINITY | 28.575000 | BASF2 | 1.66446 | 35.83 | rod (45) |  |
| 21 | INFINITY | 0.254000 | AIR |  |  |  |  |
| 22 | $c = 0.121238$ | 2.286000 | PMMA | 1.49200 | 57.40 | lens (53) |  |
|  | $k = -1.317139$ |  |  |  |  |  |  |
|  | $A = 0.269762E-04$ |  |  |  |  |  |  |
|  | $B = -0.681709E-04$ |  |  |  |  |  |  |
|  | $C = D = 0.0$ |  |  |  |  |  |  |
| 23 | −4.33469 | 0.000000 | CEMENT/AIR | 1.56000 | 44.00 |  |  |
| 24 | −4.33469 | 1.778000 | NAS30 | 1.56400 | 35.00 | lens (52) |  |
| 25 | −9.23300 | 0.254000 | AIR |  |  |  |  |
| 26 | INFINITY | 28.575000 | BASF2 | 1.66446 | 35.83 | rod (46) |  |
| 27 | INFINITY | 0.254000 | AIR |  |  |  |  |
| 28 | 9.23300 | 1.778000 | NAS30 | 1.56400 | 35.00 | lens (52) |  |
| 29 | 4.33469 | 0.000000 | CEMENT/AIR | 1.56000 | 44.00 |  |  |
| 30 | 4.33469 | 2.286000 | PMMA | 1.49200 | 57.40 | lens (53) |  |
| 31 | $c = -0.121238$ | 0.254000 | AIR |  |  |  |  |
|  | $k = -1.317139$ |  |  |  |  |  |  |
|  | $A = -0.269762E-04$ |  |  |  |  |  |  |
|  | $B = 0.681709E-04$ |  |  |  |  |  |  |
|  | $C = D = 0.0$ |  |  |  |  |  |  |
| 32 | INFINITY | 28.575000 | BASF2 | 1.66446 | 35.83 | rod (47) |  |
| 33 | INFINITY | 0.254000 | AIR |  |  |  |  |
| 34 | $c = 0.121238$ | 2.286000 | PMMA | 1.49200 | 57.40 | lens (53) |  |
|  | $k = -1.317139$ |  |  |  |  |  |  |
|  | $A = 0.269762E-04$ |  |  |  |  |  |  |
|  | $B = -0.681708E-4$ |  |  |  |  |  |  |
|  | $C = D = 0.0$ |  |  |  |  |  |  |
| 35 | −4.33469 | 0.000000 | CEMENT/AIR | 1.56000 | 44.00 |  |  |
| 36 | −4.33469 | 1.778000 | NAS30 | 1.56400 | 35.00 | lens (52) |  |
| 37 | −9.23300 | 0.254000 | AIR |  |  |  |  |
| 38 | INFINITY | 28.575000 | BASF2 | 1.66446 | 35.83 | rod (48) |  |
| 39 | INFINITY | 0.254000 | AIR |  |  |  |  |
| 40 | 9.23300 | 1.778000 | NAS30 | 1.56400 | 35.00 | lens (52) |  |
| 41 | 4.33469 | 0.000000 | CEMENT/AIR | 1.56000 | 44.00 |  |  |
| 42 | 4.33469 | 2.286000 | PMMA | 1.49200 | 57.40 | lens (53) |  |
| 43 | $c = -0.121238$ | 0.254000 | AIR |  |  |  |  |
|  | $k = -1.317139$ |  |  |  |  |  |  |
|  | $A = -0.269762E-04$ |  |  |  |  |  |  |
|  | $B = 0.681709E-04$ |  |  |  |  |  |  |
|  | $C = D = 0.0$ |  |  |  |  |  |  |
| 44 | INFINITY | 28.575000 | BASF2 | 1.66446 | 35.83 | rod (49) |  |
| 45 | INFINITY | 0.254000 | AIR |  |  |  |  |
| 46 | $c = 0.121238$ | 2.286000 | PMMA | 1.49200 | 57.40 | lens (53) |  |
|  | $k = -1.317139$ |  |  |  |  |  |  |
|  | $A = 0.269762E-04$ |  |  |  |  |  |  |
|  | $B = -0.681709E-04$ |  |  |  |  |  |  |
|  | $C = D = 0.0$ |  |  |  |  |  |  |
| 47 | −4.33469 | 0.000000 | CEMENT/AIR | 1.56000 | 44.00 |  |  |
| 48 | −4.33469 | 1.778000 | NAS30 | 1.56400 | 35.00 | lens (52) |  |
| 49 | −9.23300 | 0.254000 | AIR |  |  |  |  |
| 50 | INFINITY | 6.350000 | BASF2 | 1.66446 | 35.83 | rod (50) |  |
| 51 | INFINITY | 0.000000 | AIR |  |  |  |  |
| 52 | INFINITY | 1.000000 | BK7 | 1.51680 | 64.17 | window (56) |  |
| 53 | INFINITY | 0.254000 | AIR/WATER |  |  |  |  |
| 54 | INFINITY | 1.000000 | BK7 | 1.51680 | 64.17 | window (58) | Ocular (20) |
| 55 | INFINITY | 3.253251 | AIR |  |  |  |  |
| 56 | INFINITY | 2.540000 | AIR |  |  | int. image |  |

TABLE I-continued

| Sn | Radius (mm) or Aspheric Terms or (Tilt Angle) | Thickness (mm) | Medium | Refractive Index (Nd) | Dispersion (Vd) | Element | Assembly |
|---|---|---|---|---|---|---|---|
| 57 | INFINITY | 2.032000 | SK5 | 1.58913 | 61.27 | lens (59) | |
| 58 | 6.57332 | 2.680977 | F8 | 1.59551 | 39.18 | lens (60) | |
| 59 | −14.12584 | 22.223063 | AIR | | | | |
| 60 | INFINITY | 0.000000 | AIR | | | (aperture stop) | |
| 61 | 9.82357 | 4.572000 | SK16 | 1.62041 | 60.33 | lens (62) | |
| 62 | −3.81000 | 2.032000 | LAF2 | 1.74400 | 44.72 | lens (64) | |
| 63 | INFINITY | 3.623418 | AIR | | | | |
| 64 | 8.60409 | 3.810000 | SK5 | 1.58913 | 61.27 | lens (66) | |
| 65 | −8.60409 | 3.621807 | AIR | | | | |
| 66 | −2.90783 | 2.032000 | SF11 | 1.78472 | 25.76 | lens (68) | |
| 67 | INFINITY | 12.700000 | AIR | | | | |
| 68 | INFINITY | 2.000000 | FUSED SILICA | | | spatial fil (70) | Camera (22) |
| 69 | INFINITY | 2.350000 | BK7 | 1.51680 | 64.17 | IR filter | |
| 70 | INFINITY | 1.500000 | FUSED SILICA | | | window | |
| 71 | INFINITY | 0.000000 | AIR | | | (image plane) | |

The endoscope defined by Table I above has a field of view approximately 68° wide centered on an axis 25° from the optical axis of the probe, and a focal length of 1.3 mm in the anticipated saline environment.

Figure 13:
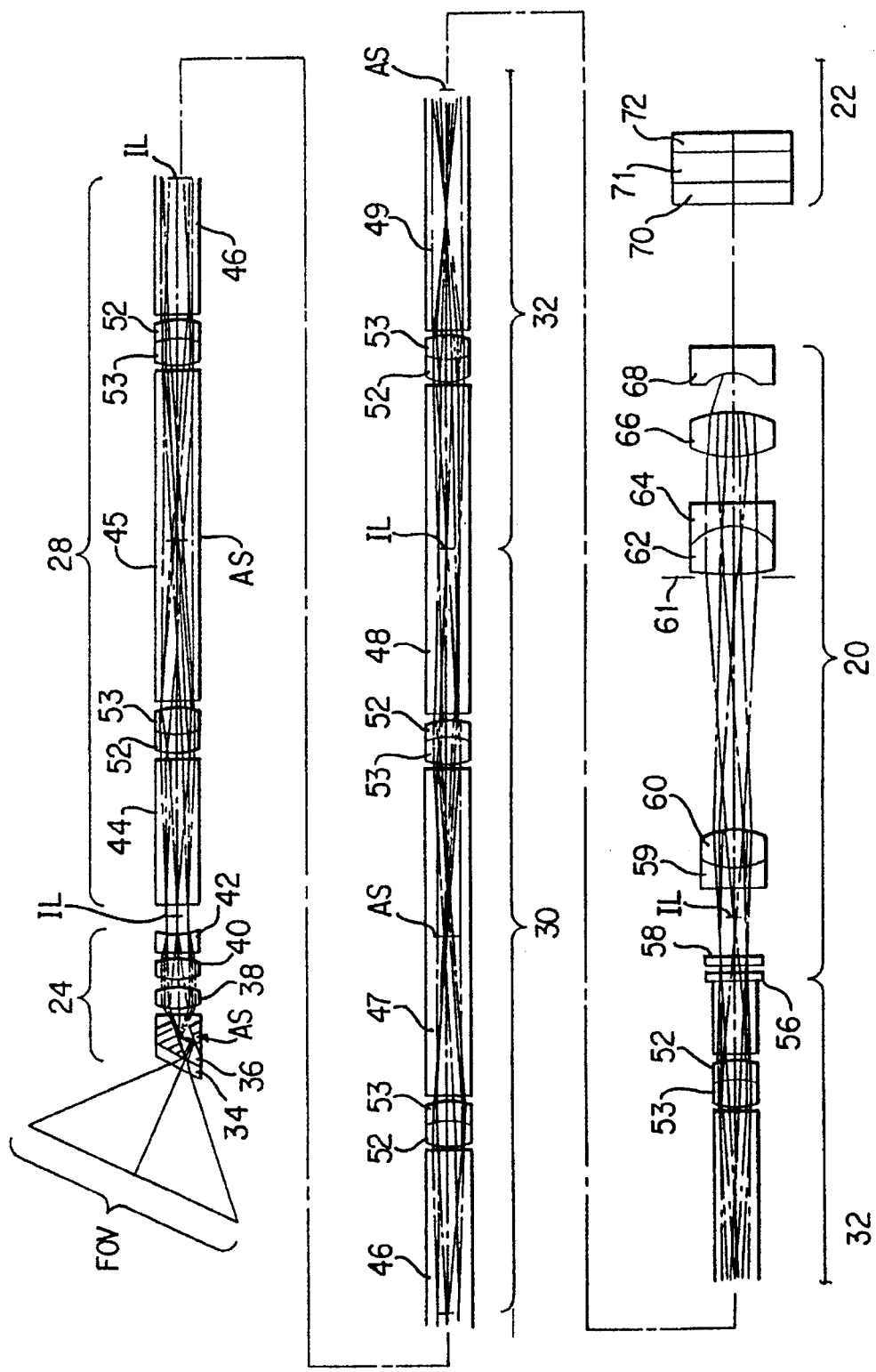
FIG. 13 is a ray-tracing diagram showing the paths of various light rays through the endoscope of the invention, illustrating the positions of intermediate images formed therein.

FIG. 13 is a complete ray-tracing diagram of the endoscope of the invention showing the respective paths through the endoscope of light rays from various portions of its field of view FOV. Light collected from the field of view FOV is formed into an image by objective 24, and the image is reformed at four intermediate image locations IL. The first intermediate image location IL is between the objective 24 and the transfer module assembly 26, as shown; the second and third intermediate image locations are between the relay modules 28 and 30, and 30 and 32, respectively; and the fourth intermediate image location is between the transfer module assembly and the ocular 20. As noted, by forming the second and third intermediate images within continuous glass rods 46 and 48 of the transfer module assembly, rather than at the surfaces of optical elements, the effect of any surface imperfections on the ultimate image is eliminated. FIG. 13 also shows the aperture stop 61; images of the aperture stop appear at locations AS within the prism 34 and at intermediate points within each relay module.

Thus, it will be appreciated that an important aspect of the method of the invention of forming a visible image of an interior of a body cavity or the like is the step of forming intermediate images between the objective and the transfer module assembly, and between each of the relay modules. Further, as discussed above, the image formed by the objective and thus transmitted to the ocular by the transfer module assembly includes certain predetermined aberration (particularly axial and lateral chromatic aberration, and field curvature) corrected by the ocular according to the method of the invention.

Numerous conventional techniques may be of use in practicing the invention. For example, it is well known to coat optical surfaces at which an air gap exists with an antireflection coating, to minimize light loss. Known multilayer dielectric coatings are preferred for this purpose; a magnesium fluoride film of approximately 137.5 nm thickness, that is, equal to one-quarter the wavelength of light in the center of the band to be collected, is also satisfactory. The circumferential surfaces of the various elements may be blackened to absorb stray light. The outer 16 peripheral surfaces of each of the elements are cylindrical, specifically 3.5 mm diameter in the embodiment described herein in detail, so that the probe may be assembled simply by inserting the elements in sequence into the bore of a tube.

These and other aspects of practice of the invention are within the skill of the art.

The design of the endoscope according to the invention having thus been specified in detail, its advantages and improvements over the prior art can now effectively be summarized.

According to an important aspect of the invention, most of the surfaces of the glass elements of the disposable probe 10 are planar. The sole exception is the spherical surface $S_2$ formed in the distal window element 34. The remaining elements of the disposable robe 10 having curved optical surfaces are inexpensively molded of plastic. While the optical elements of the ocular 20 are of glass, the ocular is not disposable so that its cost does not contribute significantly to the per-use cost of the endoscope according to the invention.

The preferred design specified above includes a number of molded plastic lenses having aspheric surfaces which are relatively easy to form using presently available technology. As noted, as glass molding technology matures, it may become desirable to mold some or all of the lenses of the probe of glass. It will be recognized that some of the aspheric surfaces could also be eliminated through use of appropriate nonhomogeneous optical materials, that is, materials exhibiting gradients in their index of refraction. Elements employing these materials are intended to be included within the claims of this application where not specifically excluded.

It will also be appreciated by those of skill in the art that the use of an integrally molded prism according to the invention provides substantial economy as compared to the complex prism fabrication techniques employed in the prior art. According to the invention, endoscopes comprising prisms molded of plastic can be manufactured at sufficiently low cost to be cost-efficient for single-patient, disposable use; in the future it may become preferable to mold the prism of glass.

In the following claims, it is to be understood that each of the optical elements (apart from the prism) includes first and second optical surfaces, that is, surfaces intersecting the optical axis. The optical surfaces of the various elements may be unambiguously identified by reference to their respective positions within the probe, for economy of language. Where the claims refer to the specific optical parameters of various elements of the probe, the elements are identified and specified as in Table I above. As used in the attached claims, the terms "optical element" and "element" are to be understood to refer to members having optical power, that is, having at least one curved surface. The term "doublet" is to be understood to refer to a combination of two such optical elements. Where aspheric surfaces of the various elements of the probe of the invention are specified numerically, the signs of the values for the aspheric constants A and B are given in relation to the sign of the curvature c of the corresponding element; that is, the signs of constants A, B and c vary with respect to the orientation of the corresponding surface, as shown by Table I.

It will be understood that reference herein to the fact that the probe of the endoscope of the invention is cost effective for single-patient disposable use should not be construed to limit the invention defined by the following claims, nor to preclude non-disposable, multiple-patient use of the invention.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A disposable probe adapted to be coupled to a predetermined focusing ocular and to therewith comprise an endoscope, said probe comprising an objective for forming a substantially uncorrected image and a transfer module assembly for presenting said uncorrected image to said predetermined focusing ocular, said objective and said transfer module each comprising a plurality of optical elements having optical power, wherein the optical elements of said objective include no more than one glass element having optical power, and the optical elements having optical power in said transfer module including only plastic elements, each of said optical elements being symmetric about an optical axis of the probe, said disposable probe introducing predetermined optical aberration into the uncorrected image presented to the focusing ocular, said predetermined aberration including at least field curvature and lateral chromatic aberration to a degree rendering the uncorrected image unusable in surgical procedures, and wherein said predetermined focusing ocular comprises lens means for correcting said predetermined aberration in said uncorrected image.

2. The disposable probe of claim 1, wherein the ocular with which said probe is to be used is defined by the following optical prescription:

| $S_n$ | Radius (mm) or Aspheric Values | Thickness (mm) | Medium | I.R. | Disp. |
|---|---|---|---|---|---|
| 56 | INFINITY | 2.540000 | AIR | | |
| 57 | INFINITY | 2.032000 | SK5 | 1.58913 | 61.27 |
| 58 | 6.57332 | 2.680977 | F8 | 1.59551 | 39.18 |
| 59 | −14.12584 | 22.223063 | AIR | | |
| 60 | INFINITY | 0.000000 | AIR | | |
| 61 | 9.82357 | 4.572000 | SK16 | 1.62041 | 60.33 |
| 62 | −3.81000 | 2.032000 | LAF2 | 1.74400 | 44.72 |
| 63 | INFINITY | 3.623418 | AIR | | |
| 64 | 8.60409 | 3.810000 | SK5 | 1.58913 | 61.27 |
| 65 | −8.60409 | 3.621807 | AIR | | |
| 66 | −2.90783 | 2.032000 | SF11 | 1.78472 | 25.76 |
| 67 | INFINITY | 12.700000 | AIR | | |
| 68 | INFINITY | 2.000000 | FUSED SILICA | | |
| 69 | INFINITY | 2.350000 | BK7 | 1.51680 | 64.17 |
| 70 | INFINITY | 1.500000 | FUSED SILICA | | |
| 71 | INFINITY | 0.000000 | AIR | | | wherein:
$S_n$ indicates the numbers of optical surfaces defined by the prescription;
I.R. indicates the index of refraction of the optical elements defined by the prescription; and
Disp. indicates the dispersion of the optical elements defined by the prescription.

3. The disposable probe of claim 1 wherein:
said objective is an objective group comprising:
a distal element at a distal tip of the probe;
a molded prism adjacent said distal element comprising a number of reflecting surfaces for providing an oblique viewing angle; and
a plurality of molded refractive elements adjacent said prism;
said transfer module assembly comprises:
one or more relay modules, each comprising:
a plano-surfaced entry rod;
a first doublet;
a plano-surfaced intermediate rod;
a second doublet;
a plano-surfaced exit rod; and
said focusing ocular comprises:
axially movable focusing lens means; and
one or more further optical elements having optical power, for correcting said predetermined aberration in said image formed by the probe.

4. The disposable probe of claim 1 wherein said focusing ocular is a non-disposable focusing ocular group having predetermined optical characteristics;
wherein said objective is an objective group comprising:
a distal element at a tip of the probe;
a molded prism adjacent said distal element comprising a number of reflecting surfaces for providing an oblique viewing angle; and
a plurality of molded refractive elements adjacent said prism for optically interfacing said prism to said transfer module assembly; and
wherein said transfer module assembly comprises one or more relay modules, each module comprising in sequence:
a plano-surfaced glass entrance rod;
a first doublet consisting of two molded lenses;
at least one plano-surfaced glass intermediate rod;
a second doublet consisting of two molded lenses; and
a plano-surfaced glass exit rod; and
wherein said non-disposable focusing ocular group comprises:
an axially movable focusing lens means; and
one or more lenses for correcting said predetermined aberration in the image formed by the disposable probe, and for presenting the image formed by said probe to means for forming a visible image.

5. The disposable probe of claim 1 wherein said transfer module assembly transfers said optical image to a non-disposable focusing ocular group corresponding to said focusing ocular, and wherein said transfer module assembly comprises one or more relay modules each comprising in sequence:
a plano-surfaced glass entrance rod;
a first doublet;
at least one plano-surfaced glass intermediate rod;
a second doublet; and
a plano-surfaced glass exit rod;
wherein at least one lens of each doublet includes at least one aspheric surface.

6. The disposable probe of claim 1 wherein said focusing ocular is an ocular group adapted to be connected to said probe, said probe being capable of forming an image of the interior of a cavity, said image formed by said probe including said predetermined optical aberration, and wherein said ocular group communicates said image to means for forming a visible image, said ocular group comprising:

one or more axially movable focusing elements; and two doublet lens groups each including two or more optical elements having optical power to compensate for said predetermined optical aberration in the image formed by said probe.

7. The probe of claim 1 wherein said objective is an objective group having a distal end and a proximal end and comprises:

a distal element at a distal end of the objective group;

a unitary molded prism for reflecting rays entering said distal element, and directing the rays along an optical axis of the probe; and at least one molded refractive lens element disposed between said prism and said proximal end of said objective group.

8. A method for providing a visible image of the interior of a body cavity to an observer in a surgical procedure, comprising the steps of:

(a) assembling an elongated endoscopic probe to a focusing ocular, said elongated probe comprising an image-forming objective and a transfer module assembly, said objective and said transfer module assembly each comprising a plurality of optical elements, the optical elements of said objective including no more than one glass element having optical power, and all optical elements having optical power in said transfer module being formed of plastic, each of said optical elements being symmetric about an optical axis of the probe;

(b) connecting said focusing ocular to means for presenting a visible image to the observer;

(c) inserting said probe through an endoscopic portal to juxtapose said objective to the interior of the body cavity;

(d) providing with said image-forming objective an uncorrected image of the interior of the body cavity;

(e) employing said transfer module assembly to transfer said uncorrected image to said focusing ocular, said uncorrected image as transferred to said focusing ocular including substantial predetermined aberration including at least lateral chromatic aberration and field curvature;

(f) employing said focusing ocular to correct the substantial predetermined aberration in said uncorrected image and to transfer a corrected image of the interior of the body cavity to said means for presenting a visible image; and (g) employing said means for presenting to present the corrected visible image of the interior of the body cavity to the observer.

9. The method of claim 8 wherein said substantial predetermined aberration of the uncorrected image transferred to said focusing ocular includes at least chromatic aberration and field cuvature present to a degree sufficient to render an uncorrected visible image corresponding to said uncorrected image unusable in said surgical procedure.

10. A method of forming an image of the interior of a body cavity and providing a visible image corresponding thereto, comprising the steps of:

inserting an elongated probe of an endoscope through a portal to juxtapose a distal tip of said probe to the interior of the body cavity;

forming an uncorrected image of the interior of the body cavity with an objective disposed at said distal tip of said probe, said objective comprising a plurality of optical elements, no more than one of said elements being formed of glass and the remainder being molded of optical plastic, each of said elements of said objective being symmetric about an optical axis of said probe, said uncorrected image including predetermined aberration intentionally designed into said objective, said predetermined aberration including at least chromatic aberration present to a degree such as to render said uncorrected image unusable in surgical procedures;

transferring, by means of an elongated transfer module assembly, said uncorrected image including said predetermined aberration from said objective to a proximal end of said probe;

forming intermediate uncorrected images including said predetermined aberration at intervals along the length of said elongated transfer module assembly and at the proximal end of said probe;

coupling an ocular to said proximal end of said probe;

transferring said uncorrected image including said predetermined aberration formed at said proximal end of said probe to said ocular;

employing said ocular to correct said uncorrected image to remove said predetermined aberration, and to thereby produce a corrected image; and displaying the corrected image on means for displaying a visible image.

11. The method of claim 10, wherein said predetermined aberration included in said image formed by said objective includes one or more of chromatic aberration, field curvature, and astigmatism.

12. The method of claim 10, wherein said intermediate images formed at intervals along the length of said elongated transfer module assembly are located within solid optical members comprised by said transfer module assembly.

13. A method of fabricating a disposable probe for providing an optical image having predetermined optical aberration, for use in combination with a focusing ocular having predetermined optical aberration correction characteristics, the combination comprising a surgical endoscope for providing a visible image substantially free of aberration, said method including the step of intentionally designing said probe to comprise a plurality of axially symmetric optical elements having optical power, no more than one optical element having optical power in said probe being formed of glass, and the remaining optical elements of said probe having optical power being formed of plastic, and the step of intentionally designing said probe to form an optical image and transmit said image to said focusing ocular, said optical image formed and transmitted by said probe including predetermined optical aberration, said predetermined optical aberration in said optical image formed and transmitted by said probe including predetermined degrees of field curvature and lateral chromatic aberration sufficient to render the transmitted optical images unusable for surgical procedures, and said predetermined optical aberration being substantially entirely corrected by said predetermined optical aberration correction characteristics of said focusing ocular.

* * * * *